United States Patent [19]

Hirabayashi et al.

[11] Patent Number: 6,054,309

[45] Date of Patent: Apr. 25, 2000

[54] CERAMIDE GLUCOSYLTRANSFERASE

[75] Inventors: Yoshio Hirabayashi; Shin-ichi Ichikawa, both of Saitama, Japan

[73] Assignee: The Institute of Physical and Chemical Research, Japan

[21] Appl. No.: 09/014,888

[22] Filed: Jan. 28, 1998

Related U.S. Application Data

[62] Division of application No. 08/663,713, Jun. 14, 1996, Pat. No. 5,780,284.

[30] Foreign Application Priority Data

Jun. 15, 1995 [JP] Japan ................................... 7-148472

[51] Int. Cl.$^7$ ............................... C12N 1/20; C12N 9/10; C12N 15/00; C12N 5/00; C07H 21/04
[52] U.S. Cl. ................ 435/252.3; 435/193; 435/254.11; 435/320.1; 435/325; 536/23.2; 536/23.5
[58] Field of Search ................................ 435/193, 320.1, 435/252.3, 254.11, 325; 536/23.2, 23.5; 935/22

[56] References Cited

U.S. PATENT DOCUMENTS 5,780,284  7/1998  Hirabayashi et al. ................... 435/193

FOREIGN PATENT DOCUMENTS 5-064584  3/1993  Japan .

OTHER PUBLICATIONS

S. Ichikawa et al., "A mouse B16 melanoma mutant deficient in glycolipids", Proc. Natl. Acad. Sci. USA, vol. 91, pp. 2703–2707, Mar., 1994.
Brian Seed et al., "Molecular cloning of the CD2 antigen, the T–cell erythrocyte receptor, by a rapid immunoselection procedure", Proc. Natl. Acad. Sci. USA, vol. 84, pp. 3365–3369, May 1987.
Shinichi Ichikawa et al., "Expression cloning of a cDNA for human ceramide glucosyltransferase that catalyzes the first glycosylation step of glycosphingolipid synthesis", Proc. Natl. Acad. Sci. USA, vol. 93, pp. 4638–4643, May, 1996.
Takakazu Kaneko et al., "Sequence Analysis of the Genome of the Unicellular Cyanobacterium *Synechocystis* sp. Strain PCC6803. II. Sequence Determination of the Entire Genome and Assignment of Potential Protein–coding Regions", DNA Research, vol. 3, pp. 109–136, 1996.
I. Durieux et al., *Glycoconjuate Journal*, 7(2), 183–192 (Apr. 1990).
*The Protein Folding Problem and Tertiary Structure Prediction*, K. Merz et al., eds., Birkhauser Boston (1994), pp. 491–495.
S. Schulte et al., *Proc. Natl. Acad. Sci. USA*, 90, 10265–10269 (Nov. 1993).
P. Paul et al., *J. Biol. Chem.*, 271(4), 2287–2293 (Jan. 1996).
S. Ichikawa et al., *Proc. Natl. Acad. Sci. USA*, 93, 4638–4643 (May 1996).
R. Vunnam et al., *Biochimica et Biophysica Acta*, 573, 73–82 (Jan. 1979).
A. Brandli et al., *J. Biol. Chem.*, 263(31), 16283–16290 (Nov. 1988).
S. Basu et al., *J. Biol. Chem.*, 243(21), 5802–5807 (Nov. 1968).
S. Ichikawa et al., *Proc. Natl. Acad. Sci. USA*, 91, 2703–2707 (Mar. 1994).
M. Nozue et al., *Int. J. Cancer*, 42, 734–738 (Apr. 1988).
N. Radin, *Neurochem. Res.*, 19(5), 533–540 (Sep. 1993).
J. Inokuchi et al., *J. Lipid Res,*, 28, 565–571 (1987).
A. Futerman et al., *Biochem. J.*, 280 295–302 (1991).
I. Durieux et al., *Biochimica et Biophysica Acta*, 1024, 263–266 (1990).
H. Lannert et al., *FEBS Letters*, 342, 91–96 (1994).
D. Jeckel et al., *J. Cell Biol.*, 117(2), 259–267 (Apr. 1992).
M. Trinchera, *J. Biol. Chem.*, 266(31), 20907–20912 (Nov. 1991).

*Primary Examiner*—Charles L. Patterson, Jr.
*Assistant Examiner*—Einar Stole
*Attorney, Agent, or Firm*—Wenderoth, Lind & Ponack, L.L.P.

[57] ABSTRACT

The subject invention provides a novel ceramide glucosyltransferase having catalytic activity of glucose transfer from UDP-Glc to ceramide, and a nucleic acid sequence encoding the ceramide glucosyltransferase.

20 Claims, 4 Drawing Sheets

```
Met Ala Leu Leu Asp Leu Ala Leu Glu Gly Met Ala Val Phe Gly   15
Phe Val Leu Phe Leu Val Leu Trp Leu Met His Phe Met Ala Ile   30
Ile Tyr Thr Arg Leu His Leu Asn Lys Ala Thr Asp Lys Gln       45
Pro Tyr Ser Lys Leu Pro Gly Val Ser Leu Leu Lys Pro Leu Lys   60
Gly Val Asp Pro Asn Leu Ile Asn Asn Leu Glu Thr Phe Phe Glu   75
Leu Asp Tyr Pro Lys Tyr Glu Val Leu Leu Cys Val Gln Asp His   90
Asp Asp Pro Ala Ile Asp Val Cys Lys Lys Leu Leu Gly Lys Tyr  105
Pro Asn Val Asp Ala Arg Leu Phe Ile Gly Gly Lys Lys Val Gly  120
Ile Asn Pro Lys Ile Asn Asn Leu Met Pro Gly Tyr Glu Val Ala  135
Lys Tyr Asp Leu Ile Trp Ile Cys Asp Ser Gly Ile Arg Val Ile  150
Pro Asp Thr Leu Thr Asp Met Val Asn Gln Met Thr Glu Lys Val  165
Gly Leu Val His Gly Leu Pro Tyr Val Ala Asp Arg Gln Gly Phe  180
```

FIG. 2B

```
Ala Ala Thr Leu Glu Gln Val Tyr Phe Gly Thr Ser His Pro Arg  195
Tyr Tyr Ile Ser Ala Asn Val Thr Gly Phe Lys Cys Val Thr Gly  210
Met Ser Cys Leu Met Arg Lys Asp Val Leu Asp Gln Ala Gly Gly  225
Leu Ile Ala Phe Ala Gln Tyr Ile Ala Glu Asp Tyr Phe Met Ala  240
Lys Ala Ile Ala Asp Arg Gly Trp Arg Phe Ala Met Ser Thr Gln  255
Val Ala Met Gln Asn Ser Gly Ser Tyr Ser Ile Ser Gln Phe Gln  270
Ser Arg Met Ile Arg Trp Thr Lys Leu Arg Ile Asn Met Leu Pro  285
Ala Thr Ile Ile Cys Glu Pro Ile Ser Glu Cys Phe Val Ala Ser  300
Leu Ile Ile Gly Trp Ala Ala His His Val Phe Arg Trp Asp Ile  315
Met Val Phe Phe Met Cys His Cys Leu Ala Trp Phe Ile Phe Asp  330
Tyr Ile Gln Leu Arg Gly Val Gln Gly Gly Thr Leu Cys Phe Ser  345
Lys Leu Asp Tyr Ala Val Ala Trp Phe Ile Arg Glu Ser Met Thr  360
Ile Tyr Ile Phe Leu Ser Ala Leu Trp Asp Pro Thr Ile Ser Trp  375
Arg Thr Gly Arg Tyr Arg Leu Arg Cys Gly Gly Thr Ala Glu Glu  390
Ile Leu Asp Val                                              394
```

६,०५४,३०९

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1347 bases
      (B) TYPE: nucleic acid
      (C) STRANDEDNESS: double
      (D) TOPOLOGY: linear    (xi) SEQUENCE DESCRIPTION: SEQ ID NO:1:

```
ATG GCG CTG CTG GAC CTG GCC TTG GAG GGA ATG GCC GTC TTC GGG          45
Met Ala Leu Leu Asp Leu Ala Leu Glu Gly Met Ala Val Phe Gly
 1               5                  10                  15

TTC GTC CTC TTC TTG GTG CTG TGG CTG ATG CAT TTC ATG GCT ATC          90
Phe Val Leu Phe Leu Val Leu Trp Leu Met His Phe Met Ala Ile
                20                  25                  30

ATC TAC ACC CGA TTA CAC CTC AAC AAG AAG GCA ACT GAC AAA CAG         135
Ile Tyr Thr Arg Leu His Leu Asn Lys Lys Ala Thr Asp Lys Gln
                35                  40                  45

CCT TAT AGC AAG CTC CCA GGT GTC TCT CTT CTG AAA CCA CTG AAA         180
Pro Tyr Ser Lys Leu Pro Gly Val Ser Leu Leu Lys Pro Leu Lys
                50                  55                  60

GGG GTA GAT CCT AAC TTA ATC AAC AAC CTG GAA ACA TTC TTT GAA         225
```

```
                                              -continued

Gly Val Asp Pro Asn Leu Ile Asn Asn Leu Glu Thr Phe Phe Glu
             65                  70                  75

TTG GAT TAT CCC AAA TAT GAA GTG CTC CTT TGT GTA CAA GAT CAT        270
Leu Asp Tyr Pro Lys Tyr Glu Val Leu Leu Cys Val Gln Asp His
             80                  85                  90

GAT GAT CCA GCC ATT GAT GTA TGT AAG AAG CTT CTT GGA AAA TAT        315
Asp Asp Pro Ala Ile Asp Val Cys Lys Lys Leu Leu Gly Lys Tyr
             95                 100                 105

CCA AAT GTT GAT GCT AGA TTG TTT ATA GGT GGT AAA AAA GTT GGC        360
Pro Asn Val Asp Ala Arg Leu Phe Ile Gly Gly Lys Lys Val Gly
            110                 115                 120

ATT AAT CCT AAA ATT AAT AAT TTA ATG CCA GGA TAT GAA GTT GCA        405
Ile Asn Pro Lys Ile Asn Asn Leu Met Pro Gly Tyr Glu Val Ala
            125                 130                 135

AAG TAT GAT CTT ATA TGG ATT TGT GAT AGT GGA ATA AGA GTA ATT        450
Lys Tyr Asp Leu Ile Trp Ile Cys Asp Ser Gly Ile Arg Val Ile
            140                 145                 150

CCA GAT ACG CTT ACT GAC ATG GTG AAT CAA ATG ACA GAA AAA GTA        495
Pro Asp Thr Leu Thr Asp Met Val Asn Gln Met Thr Glu Lys Val
            155                 160                 165

GGC TTG GTT CAC GGG CTG CCT TAC GTA GCA GAC AGA CAG GGC TTT        540
Gly Leu Val His Gly Leu Pro Tyr Val Ala Asp Arg Gln Gly Phe
            170                 175                 180

GCT GCC ACC TTA GAG CAG GTA TAT TTT GGA ACT TCA CAT CCA AGA        585
Ala Ala Thr Leu Glu Gln Val Tyr Phe Gly Thr Ser His Pro Arg
            185                 190                 195

TAC TAT ATC TCT GCC AAT GTA ACT GGT TTC AAA TGT GTG ACA GGA        630
Tyr Tyr Ile Ser Ala Asn Val Thr Gly Phe Lys Cys Val Thr Gly
            200                 205                 210

ATG TCT TGT TTA ATG AGA AAA GAT GTG TTG GAT CAA GCA GGA GGA        675
Met Ser Cys Leu Met Arg Lys Asp Val Leu Asp Gln Ala Gly Gly
            215                 220                 225

CTT ATA GCT TTT GCT CAG TAC ATT GCC GAA GAT TAC TTT ATG GCC        720
Leu Ile Ala Phe Ala Gln Tyr Ile Ala Glu Asp Tyr Phe Met Ala
            230                 235                 240

AAA GCG ATA GCT GAC CGA GGT TGG AGG TTT GCA ATG TCC ACT CAA        765
Lys Ala Ile Ala Asp Arg Gly Trp Arg Phe Ala Met Ser Thr Gln
            245                 250                 255

GTT GCA ATG CAA AAC TCT GGC TCA TAT TCA ATT TCT CAG TTT CAA        810
Val Ala Met Gln Asn Ser Gly Ser Tyr Ser Ile Ser Gln Phe Gln
            260                 265                 270

TCC AGA ATG ATC AGG TGG ACC AAA CTA CGA ATT AAC ATG CTT CCT        855
Ser Arg Met Ile Arg Trp Thr Lys Leu Arg Ile Asn Met Leu Pro
            275                 280                 285

GCT ACA ATA ATT TGT GAG CCA ATT TCA GAA TGC TTT GTT GCC AGT        900
Ala Thr Ile Ile Cys Glu Pro Ile Ser Glu Cys Phe Val Ala Ser
            290                 295                 300

TTA ATT ATT GGA TGG GCA GCC CAC CAT GTG TTC AGA TGG GAT ATT        945
Leu Ile Ile Gly Trp Ala Ala His His Val Phe Arg Trp Asp Ile
            305                 310                 315

ATG GTA TTT TTC ATG TGT CAT TGC CTG GCA TGG TTT ATA TTT GAC        990
Met Val Phe Phe Met Cys His Cys Leu Ala Trp Phe Ile Phe Asp
            320                 325                 330

TAC ATT CAA CTC AGG GGT GTC CAG GGT GGC ACA CTG TGT TTT TCA       1035
Tyr Ile Gln Leu Arg Gly Val Gln Gly Gly Thr Leu Cys Phe Ser
            335                 340                 345

AAA CTT GAT TAT GCA GTC GCC TGG TTC ATC CGC GAA TCC ATG ACA       1080
Lys Leu Asp Tyr Ala Val Ala Trp Phe Ile Arg Glu Ser Met Thr
            350                 355                 360
```

```
ATA TAC ATT TTT TTG TCT GCA TTA TGG GAC CCA ACT ATA AGC TGG      1125
Ile Tyr Ile Phe Leu Ser Ala Leu Trp Asp Pro Thr Ile Ser Trp
            365                 370                 375

AGA ACT GGT CGC TAC AGA TTA CGC TGT GGG GGT ACA GCA GAG GAA      1170
Arg Thr Gly Arg Tyr Arg Leu Arg Cys Gly Gly Thr Ala Glu Glu
            380                 385                 390

ATC CTA GAT GTA TAA CTA CAG CTT TGT GAC TGT ATA TAA AGG AAA      1215
Ile Leu Asp Val

AAAGAGAAGT ATTATAAATT ATGTTTATAT AAATGCTTTT AAAAATCTAC           1265

CTTCTGTAGT TTTATCACAT GTATGTTTTG GTATCTGTTC TTTAATTTAT           1315

TTTTGCATGG CACTTGCATC TGTGAAAAAA AA                              1347

(2) INFORMATION FOR SEQ ID NO:2:

(i) SEQUENCE CHARACTERISTICS:
        (A) LENGTH:  394 amino acids
        (B) TYPE:  amino acid
        (C) STRANDEDNESS:  single
        (D) TOPOLOGY:  linear (xi) SEQUENCE DESCRIPTION: SEQ ID NO:2:

Met Ala Leu Leu Asp Leu Ala Leu Glu Gly Met Ala Val Phe Gly
 1               5                  10                  15

Phe Val Leu Phe Leu Val Leu Trp Leu Met His Phe Met Ala Ile
                20                  25                  30

Ile Tyr Thr Arg Leu His Leu Asn Lys Lys Ala Thr Asp Lys Gln
                35                  40                  45

Pro Tyr Ser Lys Leu Pro Gly Val Ser Leu Leu Lys Pro Leu Lys
                50                  55                  60

Gly Val Asp Pro Asn Leu Ile Asn Asn Leu Glu Thr Phe Phe Glu
                65                  70                  75

Leu Asp Tyr Pro Lys Tyr Glu Val Leu Leu Cys Val Gln Asp His
                80                  85                  90

Asp Asp Pro Ala Ile Asp Val Cys Lys Lys Leu Leu Gly Lys Tyr
                95                 100                 105

Pro Asn Val Asp Ala Arg Leu Phe Ile Gly Gly Lys Lys Val Gly
               110                 115                 120

Ile Asn Pro Lys Ile Asn Asn Leu Met Pro Gly Tyr Glu Val Ala
               125                 130                 135

Lys Tyr Asp Leu Ile Trp Ile Cys Asp Ser Gly Ile Arg Val Ile
               140                 145                 150

Pro Asp Thr Leu Thr Asp Met Val Asn Gln Met Thr Glu Lys Val
               155                 160                 165

Gly Leu Val His Gly Leu Pro Tyr Val Ala Asp Arg Gln Gly Phe
               170                 175                 180

Ala Ala Thr Leu Glu Gln Val Tyr Phe Gly Thr Ser His Pro Arg
               185                 190                 195

Tyr Tyr Ile Ser Ala Asn Val Thr Gly Phe Lys Cys Val Thr Gly
               200                 205                 210

Met Ser Cys Leu Met Arg Lys Asp Val Leu Asp Gln Ala Gly Gly
               215                 220                 225

Leu Ile Ala Phe Ala Gln Tyr Ile Ala Glu Asp Tyr Phe Met Ala
               230                 235                 240

Lys Ala Ile Ala Asp Arg Gly Trp Arg Phe Ala Met Ser Thr Gln
               245                 250                 255
```

```
Val Ala Met Gln Asn Ser Gly Ser Tyr Ser Ile Ser Gln Phe Gln
            260                 265                 270

Ser Arg Met Ile Arg Trp Thr Lys Leu Arg Ile Asn Met Leu Pro
            275                 280                 285

Ala Thr Ile Ile Cys Glu Pro Ile Ser Glu Cys Phe Val Ala Ser
            290                 295                 300

Leu Ile Ile Gly Trp Ala Ala His His Val Phe Arg Trp Asp Ile
            305                 310                 315

Met Val Phe Phe Met Cys His Cys Leu Ala Trp Phe Ile Phe Asp
            320                 325                 330

Tyr Ile Gln Leu Arg Gly Val Gln Gly Gly Thr Leu Cys Phe Ser
            335                 340                 345

Lys Leu Asp Tyr Ala Val Ala Trp Phe Ile Arg Glu Ser Met Thr
            350                 355                 360

Ile Tyr Ile Phe Leu Ser Ala Leu Trp Asp Pro Thr Ile Ser Trp
            365                 370                 375

Arg Thr Gly Arg Tyr Arg Leu Arg Cys Gly Gly Thr Ala Glu Glu
            380                 385                 390

Ile Leu Asp Val (2) INFORMATION FOR SEQ ID NO:3:

(i) SEQUENCE CHARACTERISTICS:
        (A) LENGTH:  22 bases
        (B) TYPE:  nucleic acid
        (C) STRANDEDNESS:  single
        (D) TOPOLOGY:  linear (xi) SEQUENCE DESCRIPTION: SEQ ID NO:3:

ATCATATGGC GCTGGACCTG GC                                                        22

(2) INFORMATION FOR SEQ ID NO:4:

(i) SEQUENCE CHARACTERISTICS:
        (A) LENGTH:  24 bases
        (B) TYPE:  nucleic acid
        (C) STRANDEDNESS:  single
        (D) TOPOLOGY:  linear (xi) SEQUENCE DESCRIPTION: SEQ ID NO:4:

CAATCTAGCA TCAACATTTG GATA                                                      24
```

CERAMIDE GLUCOSYLTRANSFERASE

This application is a divisional of 08/663,713, filed on Jun. 14, 1996, now U.S. Pat. No. 5,780,284, and claims priority under 35 USC 119 of Japanese Application No. 148472, filed Jun. 15, 1995.

BACKGROUND OF THE INVENTION

1. Field of the Invention

The present invention relates to sugar transferases and the genes encoding said enzymes. More specifically, the present invention relates to ceramide glucosyltransferases, i.e., glucosylceramide synthetases catalyzing glucose transfer, and to genes encoding the enzymes.

2. Description of Related Art

Glycosphingolipids (GSLs) are a class of membrane components that have the lipid portion embedded in the outer leaflet of the lipid bilayer of plasma membrane and the sugar chains extended to the outer environment. Glycosphingolipids exist essentially in all of the animal cells and are suggested as being important substances responsible for various cellular processes such as differentiation, adhesion, proliferation, and cell—cell recognition (Varki, A., Glycobiology, 3, pp.97–130, 1993).

With only a few exceptions, almost all of the glycolipids are synthesized from glucosylceramide as a precursor that is produced by the transfer of glucose to ceramide. Ceramide glucosyltransferase (UDP-glucose: ceramide β 1–1' glucosyltransferase, GlcT-1, EC2.4.1.80: hereinafter in the specification, this enzyme is occasionally referred to simply as "ceramide glucosyltransferase.") catalyzes the first glycosylation step of the glycosphingolipid biosyntheses, i.e., the transfer of glucose from UDP-Glc to ceramide (Basu, S. et al., J. Biol. Chem., 243, pp.5802–5807, 1968). Glucosylceramide (GlcCer), the product of this enzyme, serves as precursors for more than 300 of glycosphingolipid biosyntheses (Radin, N. S., Nuerochem. Res., 5, pp.533–540, 1994).

GlcT-1 was first discovered from embryonic chick brain (Basu, S. et al., J. Biol. Chem., 243, pp.5802–5807, 1968). However, the properties of the enzyme have not been fully studied, because of the difficulties in assaying and purifying the enzyme. Only limited data have been published concerning GlcT-1 so far, e.g. successful solubilization of the enzyme from rat Golgi fraction (Durieux, I. et al., Biochem. Biophys. Acta, 1024, pp.263–266, 1990) and discovery of the enzymes in liver and brain each characterized by distinguishable properties (Vunnam, R. et al., Biochem. Biophys.

Acta, 573, pp.73–82, 1979). It has recently been revealed that the synthesis of GlcCer occurs at the cytosolic surface of Golgi apparatus, while other glycosylation reactions in biosynthetic pathways of glycosphingolipid take place at the lumenal side of the organelle. However, the most of enzymatic properties of the ceramide glucosyltransferases remain unknown. As for ceramide galactosyltransferase, having a similar catalytic activity, the cloning of the enzyme was reported (Schulte, S. et al., Proc. Natl. Acad. Sci. USA, 90, pp.10265–10269, 1993).

SUMMARY OF THE INVENTION

An object of the present invention is to provide ceramide glucosyltransferases derived from mammals, preferably from human. Another object of the present invention is to provide the genes encoding said ceramide glucosyltransferases.

The inventors of the present invention previously reported the isolation and characterization of a mouse melanoma B16 mutant, GM-95, deficient in ceramide glucosyltransferases (Nozue, M. et al., Int. J. Cancer, 42, pp.734–738, 1988; Ichikawa, S. et al., Proc. Natl. Acad. Sci. USA, 91, pp.2703–2707, 1994). By an expression cloning technique using the deficient mutant cell, GM-95 as a recipient cell, the inventors succeeded in isolating the cDNA encoding human ceramide glucosyltransferase (UDP-glucose; N-acylsphingosine D-glucosyltransferase, EC 2.4.1.80).

In one aspect, the present invention provides the human ceramide glucosyltransferase characterized by the amino-acid sequence (amino acids from No.1 to 394) of SEQ. ID. No.2 disclosed in the sequence listing. In another aspect, the present invention provides the gene encoding said human ceramide glucosyltransferase, and as its preferred embodiment, the ceramide glucosyltransferase gene characterized by from nucleotide No.1 to 1185 (including the terminal codon) of the nucleic acid sequence of SEQ. ID. No.1 disclosed in the sequence listing. The enzyme of the present invention has activity of catalyzing glucose transfer from UDP-Glc to ceramide.

DETAILED DESCRIPTION OF THE PREFERRED EMBODIMENTS

Besides the naturally derived human enzyme described above, any one of the enzymes, which has activity of catalyzing glucose transfer from UDP-Glc to ceramide and is characterized by a modified amino acid sequence in which the amino acid sequence defined by SEQ. ID. No.2 is inserted, deleted, and/or substituted with one or more amino acid residues, also falls within the scope of the ceramide glucosyltransferase of the present invention. Among these enzymes, naturally derived enzymes that are being expressed in mammals such as humans, monkeys, dogs, cats, cows, horses, rats, and mice are preferred.

In further aspect, the present invention also provides a class of polypeptides each of which comprises the amino acid sequence of any one of the above-described enzymes therein and has activity of catalyzing glucose transfer from UDP-Glc to ceramide. These polypeptides are characterized to have the full length of the amino acid sequence of the above-described enzyme as a part of their entire polypeptide sequences. In addition, another class of polypeptides is also provided which has activity of catalyzing glucose transfer from UDP-Glc to ceramide and comprises, as a part or the whole thereof, an amino acid sequence that is a portion of the amino acid sequence of the above-described enzyme and responsible for glucose transfer from UDP-Glc to ceramide (i.e., so called an enzymatically active domain). These polypeptides comprise, as a part or the whole thereof, the active domoin derived from the above-described enzyme as a part thereof.

For example, a polypeptide, which is obtainable by selective removing a transmembrane domain (hydrophobic domein) and ligating a resulting active domain with a signal peptide, is expected to be useful as a soluble enzyme in an extracellularly releasable form. For a determination of the hydrophobic domain, methods well known to one of ordinary skilled artisan may be applied, which include, for example, the method of Kyte et al. (Kyte. J. et al., J. Mol. Biol., 157, pp.105–132, 1982) and the method of Hopp & Woods.

According to another aspect of the present invention, nucleotide sequences encoding any one of the above-described ceramide glucosyltransferase and those encoding any one of the above polypeptides. Examples include, any one of genes encoding the above-described human ceramide glucosyltransferase and, as a preferred example thereof, the gene characterized by nucleotide No.1 to 1185 (including the terminal codon) of the nucleic acid sequence of SEQ. ID. No.1 disclosed in the sequence listing; and a modified nucleic acid sequence encoding a polypeptide capable of catalyzing glucose transfer from UDP-Glc to ceramide in which the the nucleic acid sequence of SEQ. ID. No.1 is inserted, deleted, and/or substituted with one or more nucleic acids, all of which fall within the scope of the genes of the present invention. DNA sequences comprising any one of the aforementioned nucleotide sequences as a part thereof also fall within the scope of the present invention.

Among the genes of the present invention, the gene encoding the human ceramide glucosyltransferase can readily be obtained by one of ordinary skilled in the art according to the processes detailed in the examples set out below in the specification or by referring to the disclosed processes, or alternatively, by optionally applying appropriate alterations or modifications thereto. In addition, ceramide glucosyltransferases derived from mammals other than human can also be obtained according to the exemplified processes by suitably choosing readily available experimental materials. The genes of the present invention are useful for diagnostic probes to evaluate expression of the above enzyme in a living body, as well as for the manufacture of the aforementioned enzymes and polypeptides.

In further aspect, the present invention provides a recombinant vector comprising any one of the aforementioned genes the DNA sequences, and a transformant cell that is transformed wit said recombinant vector. Types of vectors are not particularly limited and any vectors may be used so far as they are available i the art. Preferably, types of vectors may be appropriately chosen depending on a type of a host cell to be transformed. Types of host cells are also not particularly limited and any types of cells may be used, such as, procaryotic cells including bacteria, e.g. *Escherichia coli*, or eucaryotic cells including animal cells or plant cells. An expression system using vaccuro virus may also be used.

The present invention also provides a process for preparing any one of the aforementioned ceramide glucosyltransferases or any one of the polypeptides catalyzing glucose transfer from UDP-Glc to ceramide, which comprises the step of separating and isolating said enzyme or polypeptide from a cultivation mixture obtained by culturing the above-described transformant. Methods of such cultivations as well as methods for separation and isolation of the desired enzyme or polypeptide are well known in the art.

The present invention will be further detailed by referring to the following examples. However, the scope of the present invention is not limited to these examples.

B. EXAMPLES (1) Materials and Methods (a) Materials

Monoclonal antibody M2590 (anti-GM3; IgM, Hirabayashi, Y. et al., J. Biol. Chem., 260, pp.13328–13333, 1985) was purchased from Meiji Seika Co. Ltd. Tokyo, Japan. Anti-mouse IgM goat IgG fraction ($\mu$ chain specific) was obtained from Organon Technika Corporation, High fluorescent anti-mouse gamma globulin produced in goat was purchased from Antibodies Incorporated (CA, USA). Lipofectin and G418 were obtained from Life Tech. Oriental (Tokyo, Japan). The pET system was from Takara Shuzo Co., LTD. (Kyoto, Japan; Studier, F. et al., Method in Enzymol., 185, pp.60–89, 1990).

Bis-(sulfosuccinimidyl) suberate, a bifunctional cross-linker was obtained from PIERCE (IL, USA). 6-(((N-7-nitrobenz-2-oxa-1,3-diazol-4-yl)-amino)-caproyl)-sphingosine, $C_6$-NBD-Cer, was from Molecular Probes Inc. (OR, USA). pPSVE-PyE plasmid, which carries the early region of polyoma virus, was generous gift from Dr. M. Fukuda (La Jolla Cancer Research Foundation, La Jolla, Calif.; Bierhuizen, M. F. et al., Genes and Dev., 7. pp.468–478, 1993). All other reagents were of analytical grade.

(b) cDNA library

A cDNA library of a human melanoma cell line SK-Mel-28 was a gift from Dr. M. Fukuda (La Jolla Cancer Research Foundation, La Jolla, CA). The library was prepared from poly $(A)^+$ RNA by the method of Seed et al. (Seed, B. et al., Proc. Natl. Acad. Sci. USA, 84, pp.3365–3369, 1987) using pcDNAI (Invitrogen, CA) as a mammalian expression vector. The library contained $2.5 \times 10^6$ independent clones in *E. coli* strain MC1061/P3.

(c) Cell lines and culture conditions

GM-95, a B16 melanoma mutant that does not express GlcT-1, was established according to reported methods (Nozue, M. et al., Int. J. Cancer, 42, pp.734–738, 1988; Ichikawa, S. et al., Proc. Natl. Acad. Sci. USA, 91, pp.2703–2707, 1994). GM-95-PyT, a recipient cell line for transient expression, was established by cotransfection of GM-95 with pSV2neo plasmid and pPSVE-PyE plasmid (Bierhuizen, M. F. et al., Genes and Dev., 7, pp.468–478, 1993), followed by the selection with G418. The cells were ordinarily maintained in Dulbecco's modified Eagle medium, or in DMEM (Gibco Laboratories, NY) supplemented with 10% fetal calf serum (FCS) under 5% $Co_2$ (d) Isolation of a cDNA by complementation.

Plasmids that carry cDNAs were prepared from an amplified portion of the cDNA library. GM-95-PyT cells were transfected with the plasmid DNA by electroporation (Chu, G. et al., Nucleic Acids Res., 15, pp.1311–1326, 1987). Outlines of the procedures were as follows: $2 \times 10^7$ GM-95-PyT cells were washed with K-PBS$^-$ (30.8 mM NaCl, 120.7 mM KCl, 8.1 mM $Na_2HPO_4$, and 1.46 mM $KH_2PO_4$), and suspended in 400 $\mu$l of K-PBS$^-$ supplemented with 5 mM $MgCl_2$ (K-PBS$^+$). Plasmid DNA (100 $\mu$l) dissolved in 400 $\mu$l K-PBS$^+$ was added to the cell suspension and the mixture was incubated on ice for 10 min. Cells were transferred to 0.4 cm cubette and exposed to a 300 V pulse with a capacitance of 960 $\mu$F by Gene Pulsar (Bio Rad). Then, the cells were again cooled on ice.

After 10 min, the cell suspension was diluted with 5 ml of cold serum-free DMEM and incubated for 30 min at 25° C. The cells were then inoculated in culture dishes and cultured at 37° C. in DMEM supplemented with 20% FCS. A total of 1×10⁸ cells was transfected as above, and cultured in five 15 cm culture dishes. After sixty hours, the cells were detached from the plate by incubation with 5 ml per plate of PBS containing 5 mM EDTA. The cells were resuspended at a concentration of 5×10⁷ cells/ml in PBS-EDTA-NaN$_3$ (PBS containing 5% FBS, 0.02% sodium azide, and 0.5 mM EDTA) and then subjected to a reaction with M2590 mAb (20 μg/ml) for 2 hrs on ice. After the reaction, cells were washed twice with ice-cooled PBS, resuspended in PBS containing 50 mM HEPES buffer (pH 8.3) and 0.2 mM BS$_3$ at a concentration of 1×10⁷ cells/ml, and incubated for 30 min on a ice-bath.

After then, the cells were washed twice with ice-cooled PBS, resuspended in 10 ml of PBS-EDTA-NaN$_3$, and divided into five 6 cm panning plate coated with anti-mouse IgM goat IgG (μ chain specific, Wysocki, L. et al., Proc. Natl. Acad. Sci. USA, 75, pp.2844–2848, 1978). After incubation for 4 h at 25° C., non-adherent cells were removed by gentle washing with PBS-EDTA-NaN$_3$. The plasmids were extracted from the adherent cells by the method of Hirt et al. (Hirt, B., J. Mol. Biol., 26, pp.365–369, 1967) and introduced into *E. coli.*, MC1061/P3 by electroporation. The plasmids were prepared from 500 ml of 2× YT (Maniatis, T. et al., Molecular Cloning: A Laboratory Manual, Cold Spring Harbor Laboratory Press, Plainview, N.Y.), and another round of panning was performed as described above. After the second round of panning, 500 *E. coli* clones were divided into 32 pools and plasmids were prepared from each pool by mini preparation (Maniatis, T. et al. a described above).

The plasmids were introduced into GM-95-PyT cells cultured i 24 well plates by the DEAE dextran method (Sussman, D. J. et al., Mol. Cell Biol., 4, pp.1641, 1984) and the cells were cultured for 60 h. The cells were then harvested from each of the wells and the GlcT-1 activity was measured. Two pools were found to be positive The 62 individual *E. coli* clones from the positive pools were examined as described above and a ceramide glucosyltransferase cDNA was isolated. The clone was designated as pCG-1.

(e) Stable expression of GlcT-1 in GM-95 cells pCG-1 or pcDNAI was co-transfected with pSV2neo using lipofection (Felgner, P. L. et al., Proc. Natl. Acad. Sci. USA, 84, pp.7413–7417, 1987) as described below. By using 10 cm tissue culture dishes, GM-95 cells were cultured in 10 ml DMEM supplemented with 10% FCS until they reached 50% confluency. The medium was replaced with 10 ml serum-free DMEM, and then, 300 μl of water mixed with pCG-1 (60 μg), pSV2neo (6 μg), and Lipofectin (150 μg) was added to the culture. As a control, pcDNAI vector being lack of the insert was used instead of pCG-1. The next day, the cells were subjected to selection in a medium containing 800 μg/ml of G418. After two weeks, more than 100 colonies were obtained from each of the plates. The cells were detached from the plates, mixed and replaced on new plates. The cells were maintained for two months in the medium containing G418 and used for flow-cytometry or lipid analyses without cloning.

(f) Expression of GlcT-1 in *E. coli*

The cDNA from pCG-1 was cloned into the EcoRI site of Bluescript KS vector to locate BamHI site at the 3' end (pCG-2). I NdeI site was introduced at the ATG codon of the GlcT-1 open-reading frame by standard PCR methods (Felgner, P. L. et al., Proc. Natl. Acad. Sci. USA, 84, pp.7413–7417, 1987) using primers, i.e. 5'-ATCATATGGCGCTGGACCTGGC-3'(SEQ ID NO.3) and 5'-CAATCTAGCATCAACATTTGGATA-3'(SEQ ID NO.4). The resulting 300 bp-fragment was digested with HindIII and cloned into the SmaI-HindIII region of pUC119. After amplification, the fragment was recovered by digestion with KpnI and HindIII. The fragment was then ligated to 1.1 kb KpnI-HindIII fragment of pCG-2 to afford pCG-3.

Then, the full-length cDNA having NdeI and BamHI sites, that was derived from pCG-3, was cloned into *E. coli* expression vector pET-3a (Studier, F. et al., Method in Enzymol., 185, pp.60–89, 1990). The resulting plasmid pET-CG1 was transformed into the *E. coli* strain BL21 (DE3) (Studier, F. et al., ibid., 185, pp.60–89, 1990). For the expression of the cloned GlcT-1, *E. coli* cells harboring the plasmids were grown in NZCYM medium at 37° C. (Maniatis, T. et al. as described above). When cell density was reached 0.25 OD$_{600}$, isopropyl-β-thiogalactopyranoside (IPTG) was added to a final concentration of 1 mM and the cells were incubate for an additional 5 hours. After the incubation, the cells were harvested and then disrupted by sonication. 150 μg of cell lysate was used for an enzyme assay, and an incubation was performed for 7 h. Other conditions were in accordance with the standard assay conditions.

(g) Nucleotide sequence determination

The plasmid containing human GlcT-1 cDNA was treated with exonuclease III and mung bean nuclease to construct nested deletion clones of various lengths (Heinkoff, S., Gene, 28, pp.351–359, 1984). Nucleotide sequences were determined in both directions by either the dideoxynucleotide chain termination method using BucaBEST (Takara Shuzo, Co., LTD, Kyoto, Japan; Sanger, F., et al. Proc. Natl. Acad. Sci. USA, 74, pp.5463–5467, 1977) or the cycle sequencing methods using Taq DNA polymerase. Applied Biosystems model 373 A and Pharmacia A.L.F.DNA sequencers were used for the analyses. Some analyses were performed at the Takara Shuzo custom service center.

(h) DNA manipulation

DNA manipulation was carried out according to the method of Maniatis et al. (Maniatis, T., as described above).

(i) Flow cytometry

Cells were detached from culture dishes using PBS containing 5 mM EDTA and then reacted with M2590 mAb (20 μg/ml in PBS-EDTA-NaN$_3$) for 2 h on an ice bath. The cells were washed with PBS and reacted with FITC labeled anti-mouse immunoglobulin for 3 h on ice. After washing with PBS, the cells were analyzed by FACStar (product of Becton Dickinson).

(j) Lipid analyses

Cells were collected by scraping at subconfluency, washed twice with PBS and lyophilized. Total lipids were extracted with 2( volumes of chloroform:methanol (2:1, v/v), filtered, and concentrated to dryness under reduced pressure. The total lipids were then again dissolved in a small volume of chloroform:methanol (2:1, v/v) and chromatographed on a precoated silica-gel TLC plate (E. Merck) using chloroform:methanol:water (65:25:4, v/v) Glycosphigolipids (GSLs) were visualized with orcinol-HCl reagent (k) Enzyme assay GlcT-1 activity was assayed according to the method of Lipsky et al. (Lipsky, N. G. et al., J. Cell. Biol., 100, pp.27–34, 1986) with slight modifications. C$_6$-NBD-Cer, a synthetic fluorescent substrate, in a form of liposome was used for the assay. C$_6$-NBD-Cer (50 μg) and lecithin (500 μg) were mixed in 100g 1 ethanol and the solvent was removed to dryness. After 1 ml of water was added to the residue, liposomes were prepared by sonication. A standard reaction mixture [100 μl; 20 mM Tris-HCl (pH 7.5)/500, M UDP-Glc/20 μl liposomes/50 μg cell protein as enzyme source] was incubated 4 h at 30° C. After then, lipids were extracted and applied on silica-gel 60 plates. NBD lipids were separated by using $CHCl_3/CH_3OH/H_2O$ (65:25:4, v/v) and the lipids were visualized by illumination.

(l) Protein assay

Proteins were assayed using Micro BCA Protein Assay Reagent Kit (PIERCE, Ill., USE) according to the method of Smith et al. (Smith, P. K., et al., Anal. Biochem., 150, pp.76–85, 1985). (m) Isolation of mRNA and Northern blot analysis Poly $A^+$ RNA from each cell line was isolated by Fast Track mRNA Isolation Kit (Invitrogen Corporation) according to the manufacture's instruction. Poly A+RNA (2 μg) was subjected to electrophoresis on 1% agarose gel containing formaldehyde and transblotted onto nylon membrane (Hybond-N, Amersham, Maniatis, T. et al., as described above). A pre-made membrane was used for the analysis of mRNA from various tissues (Human Multiple Tissue Northern Blot, Clontech).

The 1.1 kb HindIII-XhoI cDNA fragment of pCG-1 was labeled with $[\alpha^{-32}P]$ dCTP (6000 Ci/mmol, Amersham) by Multiprime DNA labelling system (Amersham) and used as a probe. Hybridization was carried out at 42° C. for 24 h in 5× SSPE [1× SSPE contains 0.18 M NaCl, 10 mM $NaPO_4$ (pH 7.7) and 1 mM EDTA] containing 50% formalhyde, 2% SDS, 10× Denhart's solution, 100 μg/ml of salmon sperm DNA, and $^{32}P$ labeled probe. After hybridization, the membrane was washed with 2× SSC containing 0.5% SDC and 0.1× SSC each for 40 min at 50° C.

(2) Results (a) cDNA cloning

By using a mammalian expression cloning system developed by Seed et al. (Seed, B. et al., Proc. Natl. Acad. Sci. USA, 84, pp.3365–3364, 1987), cDNAs from a SK-Mel-28 library in the expression vector peDNAI were introduced in GM-95-PyT that lacks GlcT-1 activity. The recipient cell line GM-95-PyT, GM-95 stably expressing polyoma large T antigen, allows episomal replication of transfected plasmids. Although GM-95-PyT are deficient in GlcT-1, other enzymes involved in glycosphingolipid syntheses retained their enzymatic activities. Thus, the complementation of the GlcT-1 cDNA restores the expression of GlcCer, LacCer, and GM3 that are expressed in the parental cell line.

Three days after the transfection, cells expressing GM3 were selected by panning with the anti-GM3 mAb and petri dishes coated with anti-mouse-IgM. The binding between the mAb and GM3 was not strong enough to hold the cells on the plate, and accordingly, the bound mAb and cell surface proteins were cross-linked before the panning. Plasmids were isolated from the adherent cells and elecroporated into E. coli for further amplification. After the second round of transfection, selection, and amplification, E. coli colonies were divided into subpools and screened by a sibling selection based on the enzyme assay until a single clone pCG-1 was isolated.

(b) Transient expression of GlcT-1 activity in the mutant cells

The mutant cells transfected with pCG-1 were assayed for the GlcT-l activities using $C_6$-NBD-ceramide as a substrate. SK-Mel-28 cells; SK-Mel-28 cells with no UDP-Glc addition; MEB-4 cells; MEB-4 cells with no UDP-Glc addition; GM-95-PyT cells; GM-95-PyT cells with no UDP-Glc addition; GM-95-PyT cells transfected with pcDNA I; GM-95-PyT cells transfected with pcDNA I with no UDP-Glc addition GM-95-PyT cells transfected with pCG-1; GM-95-PyT cells transfected with pCG-1 with no UDP-Glc addition; $C_6$-NBD-Cer (100 pmoles); $C_6$-NBD-GlcCer (100 pmoles); and $C_6$-NBD-SM (100 pmoles) were subjected to simultaneous analysis.

As a result, GlcT-1 activity was detected in GM-95-PyT cells transfected with pCG-1, but not detected in the cells transfected with the pcDNAI vector. The production of $C_6$-NBD-GlcCer was found to be UDP-Glc dependent. GlcT-1 activities were also detected in SK-Mel-28 cells from which the library was derived as well as in the parental cell line MEB-4. A low level of NBD-GlcCer synthesis was detected due to endogenous UDP-Glc in the lysates from these two cell lines without the addition of UDP-Glc.

(c) Restoration of glycosphingolipid expression in the mutant cells introduced with the GlcT-1 cDNA.

Expression of glycosphingolipid was first analyzed by flow cytometry using anti-GM3 mAb. Although a significant shift of main peak and a small population of strongly stained cells were observed in GM-95-PyT cells transfected with pCG-1, the ratio of positive population was relatively low. This was mainly due to the low transfection efficiency of GM-95-PyT cells. Accordingly, in order to produce GM-95 cells expressing GlcT-1 stably, GM-95 cells were co-transfected with pCG-1 and pSV2neo and selected with G418 for neomycin resistance, and as a result, more than 100 colonies were obtained. The cells were mixed and expanded for glycosphingolipid analysis without cloning. 75% of the cells were positively stained with GM3, and 15% were stained stronger than the parental cells.

Glycosphingolipids of the neomycin resistant cells were further analyzed by TLC followed by orcinol/$H_2SO_4$ reaction. The total lipids from 106 cells were spotted onto silica-gel plate and developed with a solvent (chloroform:methanol:water=65:25:4, v/v). SK-Mel-28 cells; MEB-4 cells; GM-95 cells; GM-95 cells cotransfected with pcDNA I and pSV2neo; GM-95 cells cotransfected with pCG-1 and pSV2neo; GlcCer (2 μg); LacCer (1 μg); and GM3 (1 μg) were simultaneously analyzed, and glycosphingolipids were visualized with orcinol/$H_2SO_4$ reagent. GlcCer and GM3 were detected in the total lipids extracted from GM-95 cells carrying pCG-1 but not from the cells carrying pcDNAI.

(d) Expression of enzymatically active GlcT-1 in E. coli.

In order to demonstrate that the isolated cDNA encodes the desired ceramide glucosyltransferase, per se, and that it does not encode a regulatory protein required for the expression of GlcT-1 activity, enzymatically active GlcT-l was expressed in E. coli that is not capable of expressing GlcT-1 and sphingolipids including glycosphingolipids. pET3a/BL21 (DE3); pET3a/BL21 with no UDP-Glc addition; pET3a-CGl/BL21 (DE3); pET3a-CG1/BL21 (DE3) with no UDP-G. addition; $C_6$-NBD-Cer (40 pmoles); and $C_6$-NBD-GlcCer (40 pmoles) were simultaneously analyzed. As a result, the GlcT-1 activity was detected in the cells transformed with pET-CG-1. The production of $C_6$-NBD GlcCer was observed as being UDP-Glc dependent, and no activity was detected in the cells that carried pET3a vector alone From these results, it is apparent that the above-mentioned cDNA encodes GlcT-1.

(e) Primary structure of GlcT-1.

Figure 1:
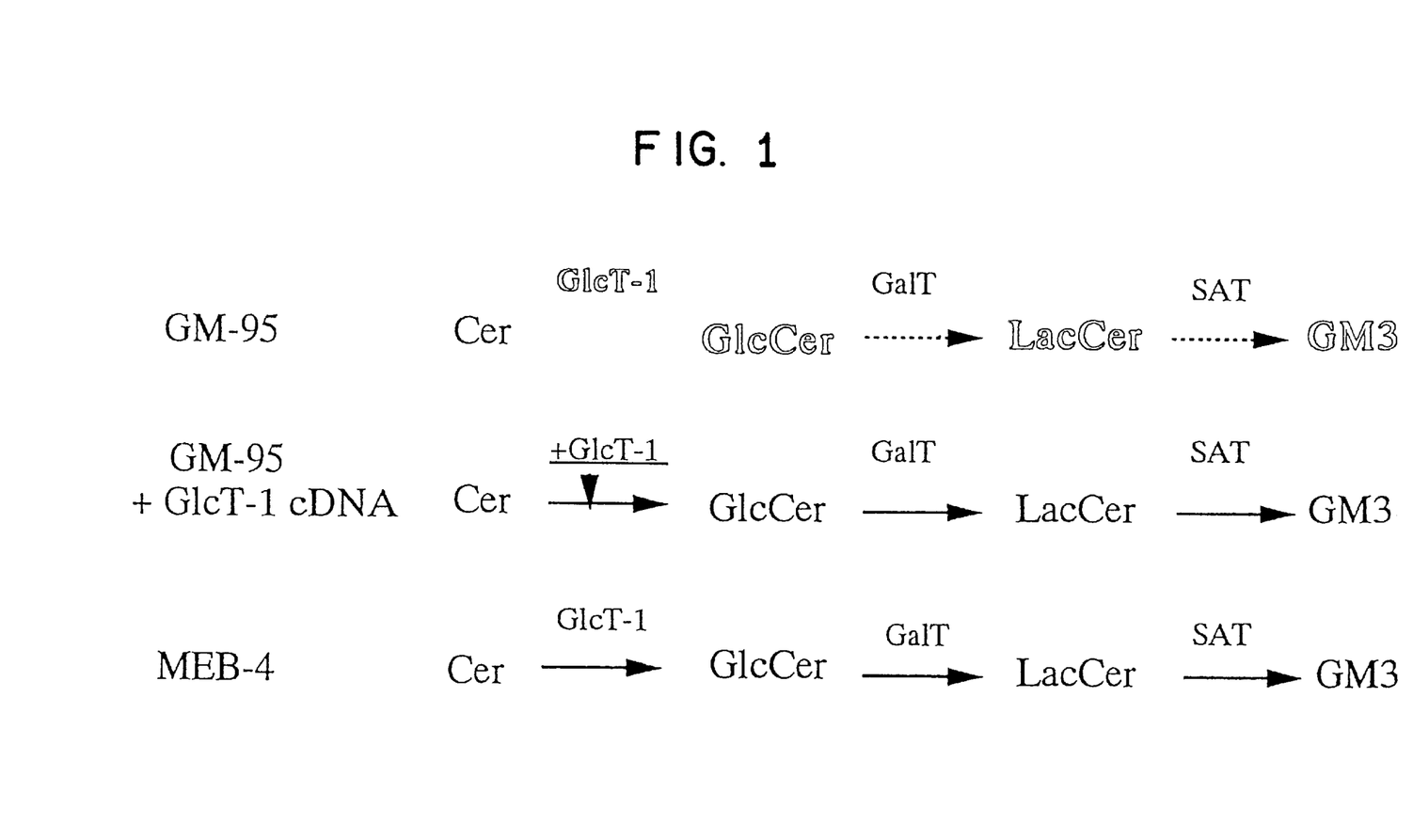
FIG. 1 shows the synthetic pathway of glycosphingolipids. Open letters indicate enzymes and glycosphingolipids deficient in GM-95cells. Broken arrows represent reactions that do not proceed in GM-95 cells due to the deficiency of substrates. Cer, ceramide; GalT, UDP-galactose: glucosylceramide galactosyltransferase; and SAT, CMP-sialic acid: lactosylceramide sialyltransferase.
Figure 2A:
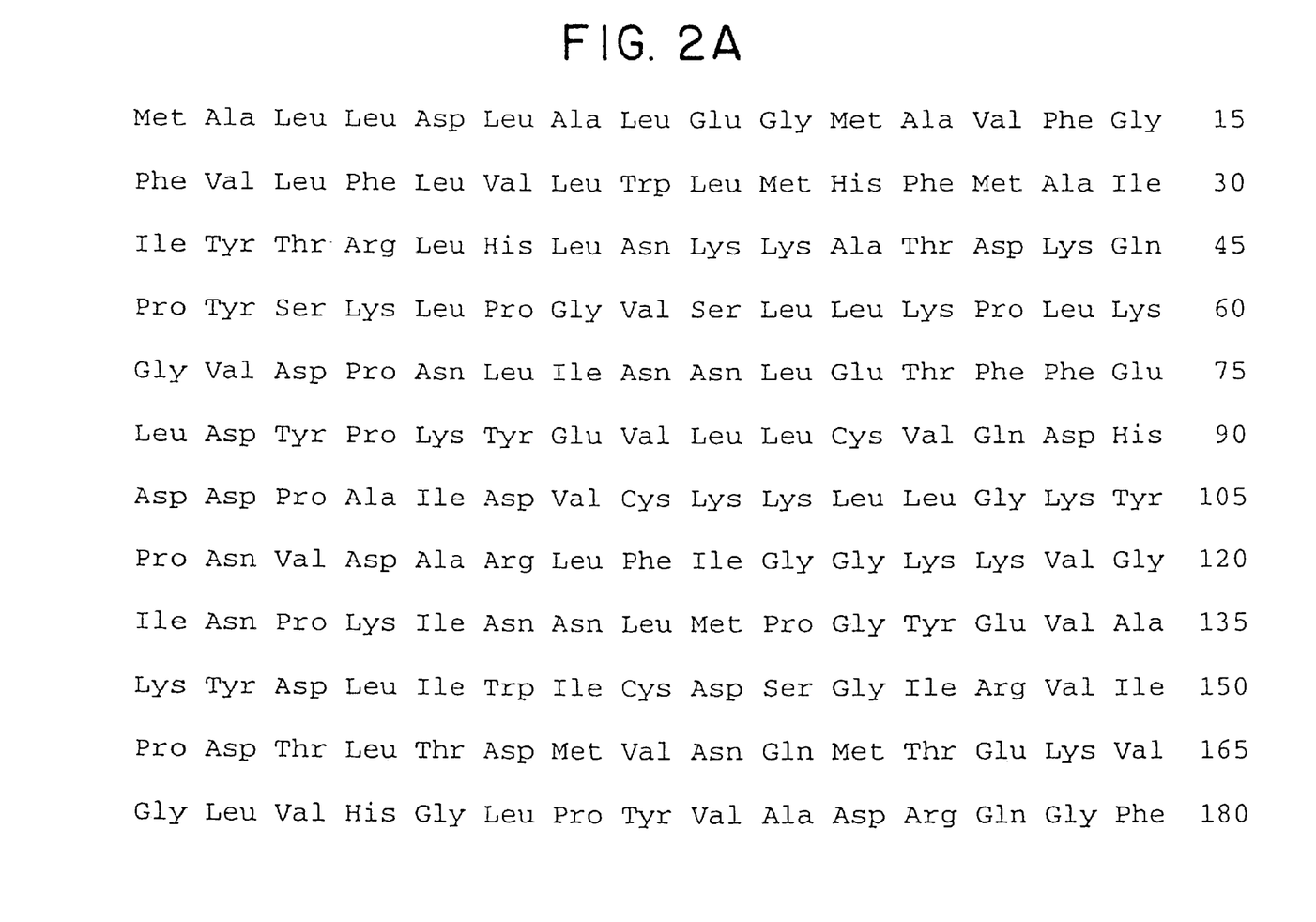
FIG. 2(A) and FIG. 2(B) shows the amino acid sequence of the human GlcT-1 as a preferred embodiment of the ceramide glucosyltransferase of the present invention.
Figure 2B:
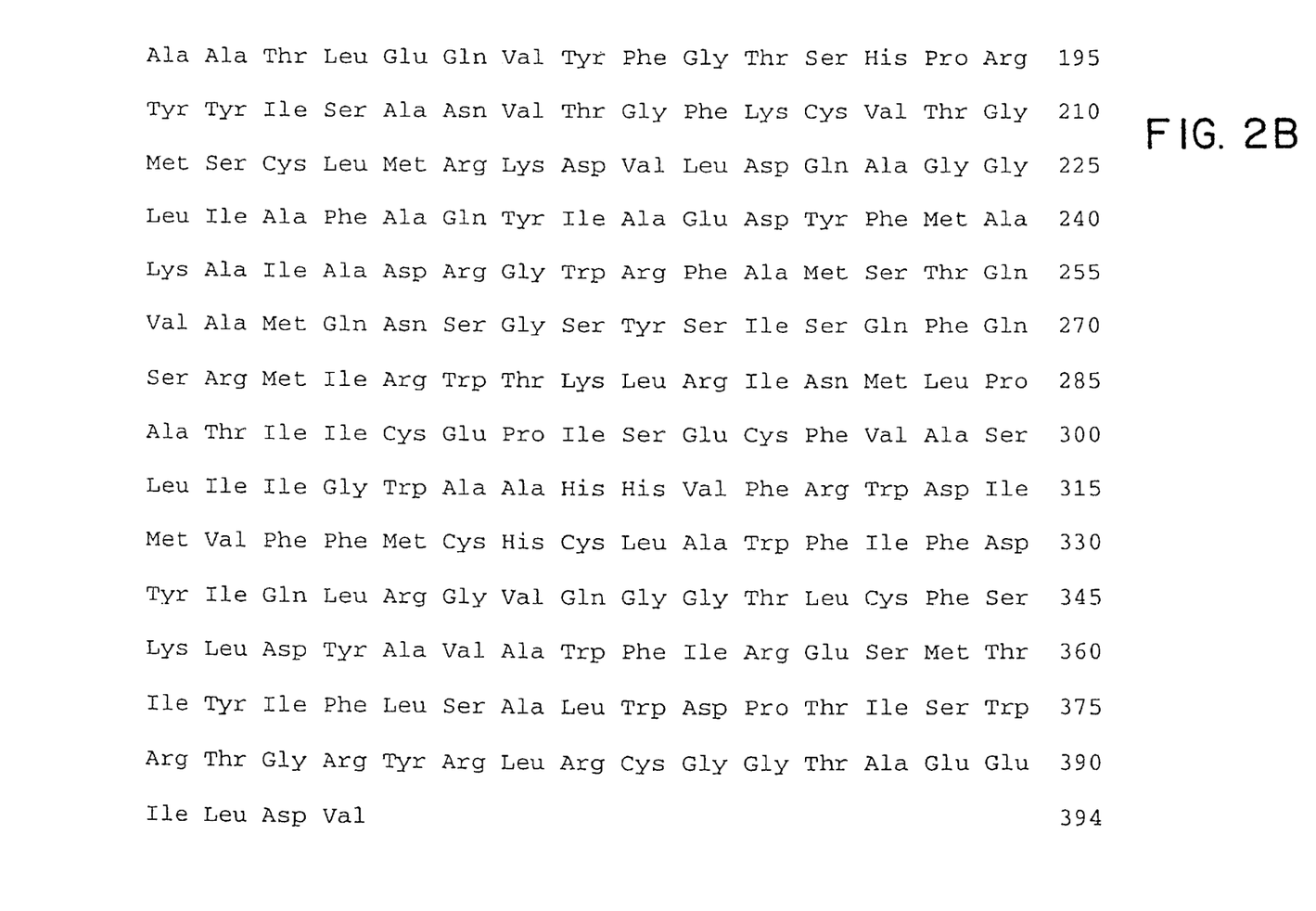

FIG. 2(A) and FIG. 2(B) show the primary amino acid sequence of GlcT-1 deduced from nucleotide sequence of the cDNA. GlcT-1 consists of 394 ami acids and has a calculated molecular mass of 44,853 dalton. No significant homologies with GlcT-1 were found by searches of the DNA and protein data bases (GenBank and PIR), which revealed that GlcT-1 is a novel protein. The GC-rich sequence that precedes to the initiation codon is presumably a part of CpG island sequence that surrounds the promoters of housekeeping genes (Bird, A. P., Nature, 321, pp.209–213, 1986). The genes that contain the above sequence are usually essential for cell viability and are expressed in most cells.

The enzyme with a similar catalytic activity, ceramide galactosyltransferase (CGT), has recently been cloned (Schulte, S. et al., Proc. Natl. Acad. Sci. USA, 90, pp.10265–10269, 1993). The sequence analysis of this enzyme revealed that the enzyme was homologous to glucuronyltransferases that are participated in drug metabolic pathways. Since GlcT-1 and CGT catalyze similar reactions, it may be worth considering a possibility that these enzymes are homologous. However, no significant sequence homology was observed, which suggests that these two enzymes have different evolutional origins. The glucuronyltransferases are expressed at the lumenal side of endoplasmic reticulam (Drake, R. R. et al., J. Biol. Chem., 267, pp.11360–11365, 1992). In contrast, GlcT-1 is a single enzyme that catalyzes the above reaction on the cytoplasmic surface, which may also support this hypothesis.

Figure 3:
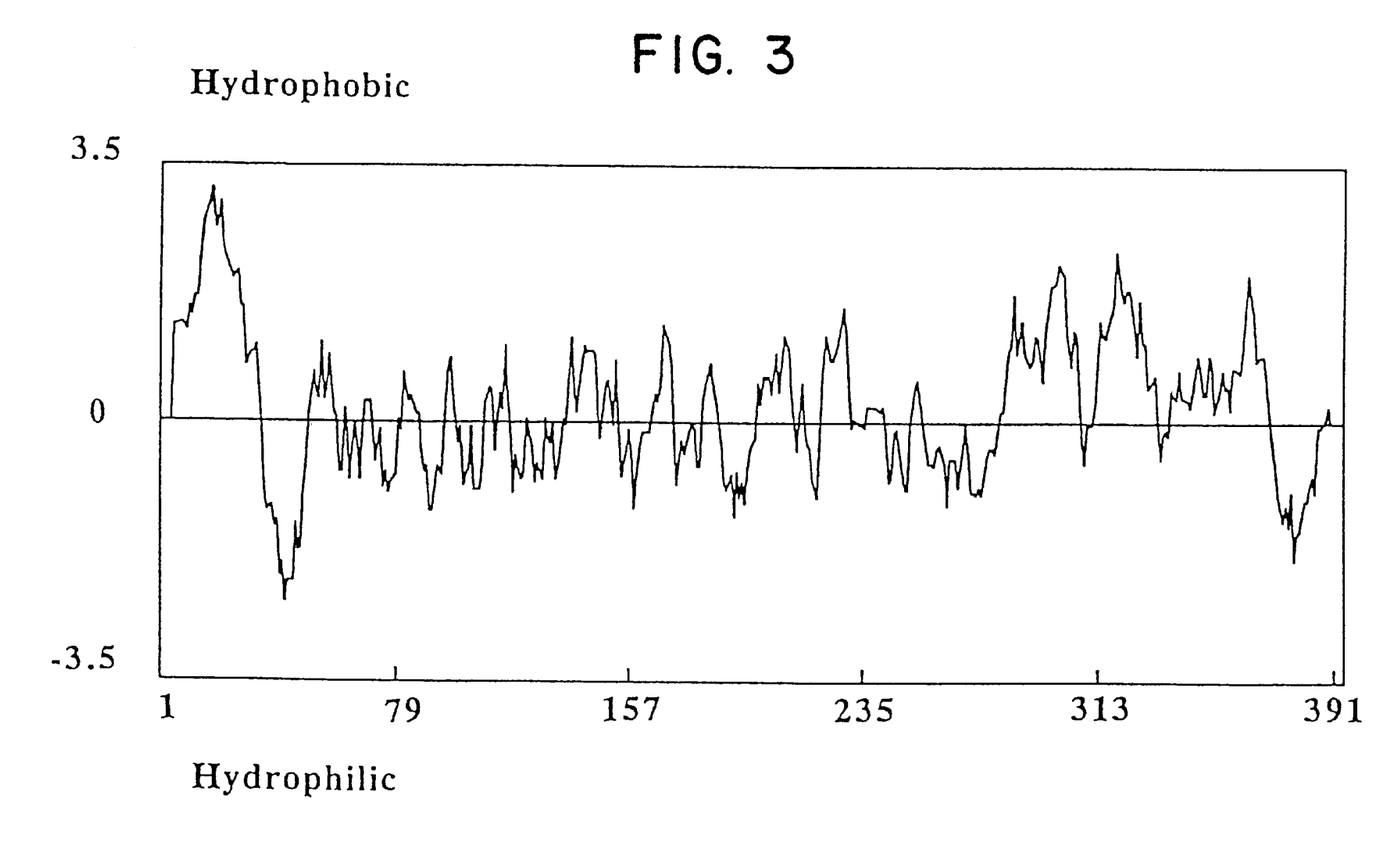
FIG. 3 shows hydropathy plot of the amino acid sequence of the human GlcT-1 as a preferred embodiment of the ceramide glucosyltransferase of the present invention. In the figure, positive values represent increased hydrophobicity and negative values increased hydrophilic

The hydropathy plot analysis (Kyte, J. et al., J. Mol. Biol. 157, pp.105–132, 1982) proved the presence of a hydrophobic segment near the N terminus that is the potential membrane-anchoring domain In addition, the considerable hydrophobicity was detected in the regions close to the C terminus, that may locate in the membrane.

(f) Northern blot analysis of GlcT-1 mRNA

The expression of GlcT-1 mRNA in melanoma cells and various human, tissues was analyzed by Northern blot analysis (poly A$^+$ RNA, 2 μg). (A) the melanoma cell lines: SK-Mel-28; MEB-4; and GM-95; an( (B) human tissues: heart; brain; placenta; lung; liver; skeletal muscle; kidney; and pancreas were subjected to a simultaneous analysis.

Hybridization with human glyceraldehyde 3-phosphate dehydrogenase (G3PDH) cDNA was carried out as control experiments. A single transcript of 3.5 kb was detected in all of the cells and tissues examined. Strong expressions of GlcT-1 mRNA were detected in SK-Mel-28 and MEB-4 cells. Due to the deficiency of the GlcT-I, a very faint band was observed in GM-95 cells. As for human tissues, GlcT-1 mRNA expressions were observed in all of the tissue examined. In control experiments, strong expression of G3PDH mRNA was observed in skeletal muscle and heart as reported previously (Vincent, S. et al., Nucleic Acids Res., 21, pp.1498, 1993).

The ceramide glucosyltransferases of the present invention are responsible for the initial glycosylation step of glycosphingolipid biosynthesis in mammals, preferably in human. They have properties to catalyze the transfer of glucose from UCP-Glc to ceramide to afford glucosylceramide. Accordingly, the enzymes of the present invention are essential for life maintenance of mammals and are extremely valuable enzymes. In addition, the enzymes of the present invention are also useful as laboratory usable agents in the fields of biochemistry and biotechnology, as well as preparatory agents for the manufacture of pharmacologically active substances Furthermore, they are expected to be useful as medicament for therapeutic and preventive treatment for various diseases based on reduced expression of said enzyme. The genes of the present invention are useful for a mass preparations of the above enzymes in highly purified forms, and also useful as probes that can be used for clinical tests and diagnosis of diseases based on abnormal expression of the above enzyme.

An example of the gene and the expression product thereof according to the present invention will be described in the sequence listings set out below.

What is claimed:

1. An isolated polynucleotide encoding a ceramide glucosyltransferase having the amino acid sequence of SEQ ID NO:2, or an enzymatically active fragment thereof.

2. The polynucleotide according to claim 1, having the nucleotide sequence according to SEQ ID NO:1.

3. The polynucleotide according to claim 1, which encodes a ceramide glucosyltransferase having the amino acid sequence of SEQ ID NO:2.

4. An isolated polynucleotide encoding a polypeptide comprising a fragment of the amino acid sequence of SEQ ID NO:2 which possesses ceramide glucosyltransferase activity.

5. An isolated polynucleotide comprising a fragment of the nucleic acid sequence of SEQ ID NO:1 and encoding a polypeptide which possesses ceramide glucosyltransferase activity.

6. The polynucleotide according to claim 1, which encodes a fragment of the amino acid sequence of SEQ ID NO:2 which possesses ceramide glucosyltransferase activity.

7. An isolated polynucleotide encoding a polypeptide comprising a fragment of the amino acid sequence of SEQ ID NO:2 which possesses ceramide glucosyltransferase activity together with at least one signal peptide.

8. An isolated polynucleotide which (1) encodes a ceramide glucosyltransferase, and (2) hybridizes to either the nucleic acid sequence of SEQ ID NO:1, or its complement, or a nucleic acid sequence encoding the amino acid sequence of SEQ ID NO:2, or its complement, under hybridization conditions of 24 hours at 42° C. in a buffer comprising 5× SSPE, 50% formaldehyde, 2% SDS, 10× Denhart's solution, and 100 $\mu$g/ml of salmon sperm DNA, and wash conditions of 2× SSC containing 0.5% SDC and 0.1× SSC each for 40 min at 50° C.

9. An isolated polynucleotide which (1) encodes a polypeptide having ceramide glucosyltransferase activity and (2) hybridizes to either a fragment of the nucleic acid sequence of SEQ ID NO:1, or its complement, or a fragment of a nucleic acid sequence encoding the amino acid sequence of SEQ ID NO:2, or its complement, under hybridization conditions of 24 hours at 42° C. in a buffer comprising 5× SSPE, 50% formaldehyde, 2% SDS, 10× Denhart's solution, and 100 µg/ml of salmon sperm DNA, and wash conditions of 2× SSC containing 0.5% SDC and 0.1× SSC each for 40 min at 50° C.

10. A vector comprising the polynucleotide of claim 1.
11. A vector comprising the polynucleotide of claim 4.
12. A vector comprising the polynucleotide of claim 5.
13. A vector comprising the polynucleotide of claim 8.
14. A vector comprising the polynucleotide of claim 9.
15. The vector of claim 10, wherein said vector is a plasmid based vector or viral based vector.
16. A host cell transformed or transfected with the vector according to claim 10.
17. A host cell transformed or transfected with the vector according to claim 11.
18. A host cell transformed or transfected with the vector according to claim 12.
19. A host cell transformed or transfected with the vector according to claim 13.
20. A host cell transformed or transfected with the vector according to claim 14.

* * * * *